(12) United States Patent
Silberstein

(10) Patent No.: US 7,454,243 B2
(45) Date of Patent: Nov. 18, 2008

(54) APTITUDE TESTING

(75) Inventor: Richard Bernard Silberstein, Blackburn (AU)

(73) Assignee: SSPT Pty Ltd., Blackburn (AU)

( * ) Notice: Subject to any disclaimer, the term of this patent is extended or adjusted under 35 U.S.C. 154(b) by 120 days.

(21) Appl. No.: 10/568,650

(22) PCT Filed: Aug. 18, 2004

(86) PCT No.: PCT/AU2004/001100

§ 371 (c)(1),
(2), (4) Date: Feb. 16, 2006

(87) PCT Pub. No.: WO2005/018449

PCT Pub. Date: Mar. 3, 2005

(65) Prior Publication Data

US 2006/0184058 A1 Aug. 17, 2006

(30) Foreign Application Priority Data

Aug. 21, 2003 (AU) .............................. 2003904477

(51) Int. Cl.
*A61B 5/00* (2006.01)
(52) U.S. Cl. ........................................ 600/544; 600/300
(58) Field of Classification Search ....................... None
See application file for complete search history.

(56) References Cited

U.S. PATENT DOCUMENTS

| | | | |
|---|---|---|---|
| 3,809,069 A * | 5/1974 | Bennett | 600/544 |
| 5,295,491 A | 3/1994 | Gevins | |
| 5,331,969 A * | 7/1994 | Silberstein | 600/544 |
| 6,416,472 B1 * | 7/2002 | Cady et al. | 600/300 |
| 6,434,419 B1 | 8/2002 | Gevins et al. | |
| 6,579,233 B2 * | 6/2003 | Hursh | 600/300 |
| 6,993,381 B2 * | 1/2006 | Connolly et al. | 600/544 |
| 2006/0064028 A1 * | 3/2006 | Amidzic | 600/544 |

FOREIGN PATENT DOCUMENTS

WO WO 01/60253 A1 8/2001

* cited by examiner

*Primary Examiner*—Robert L Nasser
(74) *Attorney, Agent, or Firm*—Wolf, Greenfield & Sacks, P.C.

(57) ABSTRACT

A method of assessing the cognitive aptitude of a subject to a predetermined task, the method including the steps of: (i) presenting to the subject a group of cognitive tasks; (ii) detecting brain response signals from the subject during presentation of the group of cognitive tasks; (iii) calculating SSVEP amplitude, phase and/or coherence responses from the brain response signals; and (iv) comparing the SSVEP responses to known SSVEP responses obtained from individuals with high and/or low aptitudes to the predetermined task in order to assess the subject's aptitude for the predetermined task.

12 Claims, 5 Drawing Sheets

APTITUDE TESTING

FIELD OF THE INVENTION

The present invention relates generally to the field of aptitude testing, including apparatus and methods for testing the aptitude of subjects to mental tasks and assessing subjects thinking style.

BACKGROUND OF THE INVENTION

Existing commonly-used aptitude tests attempt to measure a subject's current abilities using a standardised test appropriate to the subject's age, language, culture and educational background. The tests do not necessarily identify potential aptitude in subjects who do not meet a basic requirement of the tests such as a particular educational background or for whom no standardised test exists or is appropriate. For example, as existing tests require a minimum level of knowledge before aptitude can be assessed, those subjects with natural abilities not meeting the minimum requirements would generally not be identified as potential candidates. Furthermore, minorities may consider certain tests to be unfair and discriminatory. There is a need for a new test which can be used to assess potential aptitude as well as current aptitude levels.

Aptitude and thinking style are closely related and thus a test that can identify aptitude can also be used to identify a subject's thinking style. Knowledge of a subject's thinking style can also be used to identify the optimum teaching and training approach for the subject.

U.S. Pat. Nos. 4,955,938 and 5,331,969 (the contents of which are hereby incorporated herein by reference) disclose techniques for obtaining a steady state visually evoked potential (SSVEP) from a subject. These patents disclose the use of Fourier analysis in order to rapidly obtain the SSVEP's and changes thereto.

SUMMARY OF THE INVENTION

It is now appreciated that these techniques can be utilized to measure brain activity and assess the aptitude of an individual.

More particularly the invention provides a method of assessing the cognitive aptitude of a subject to a predetermined task, the method including the steps of:

(i) simultaneously presenting to the subject one of a group of cognitive tasks and a visual flicker;
(ii) detecting brain response signals from the subject during presentation of said cognitive task and visual flicker;
(iii) calculating amplitude, phase and/or coherence of SSVEP responses elicited by the visual flicker from said brain response signals; and
(iv) comparing said SSVEP responses to known SSVEP responses obtained from individuals with high and/or low aptitudes to said predetermined task in order to assess the subject's aptitude for said predetermined task.

The invention also provides an apparatus for assessing the cognitive aptitude of a subject to a predetermined task, the apparatus including:

(i) means for simultaneously presenting to the subject one of a group of cognitive tasks and a visual flicker;
(ii) means for detecting brain response signals from the subject during presentation of said cognitive task and visual flicker; (iii) means for calculating amplitude, phase and/or coherence of SSVEP responses elicited by the visual flicker from said brain response signals; and (iv) means for comparing said SSVEP responses to known SSVEP responses obtained from individuals with high and/or low aptitudes to said predetermined task in order to assess the subject's aptitude for said predetermined task.

The present invention can utilise Steady State Probe Topology (SSPT), a brain imaging technique based on the brain's response to a continuous sinusoidal visual flicker or the SSVEP to examine changes in the activity in various brain regions while an individual undertakes a number of cognitive tasks. The cognitive aptitude will be indicated by specific changes in SSVEP amplitude, phase and coherence during a given cognitive task. The changes in SSVEP amplitude, phase and coherence can also indicate different thinking styles associated with different patterns of brain activity. Subjects that score high, on a test of analytical thinking show greater left hemisphere phase advance that is interpreted as greater activation of this area during the analytical task. By contrast, subjects that score low on the test of analytical thinking do not show this pattern. In addition, subjects that score high on a test of holistic thinking show greater SSVEP phase advance at right hemisphere sites. These results are consistent with neuropsychological research indicating a specialised role for the left hemisphere in analytical thinking and the right hemisphere for holistic thinking.

More generally, SSVEP can be used to identify aptitude in specific cognitive domains known to be associated with performance and training aptitude. For example, trainee aircraft pilots need aptitude in visualizing their environment in three dimensions. A test for this ability could involve SSVEP measurements while the subject undertakes the Mental Rotation Task where they are required to rotate images of three dimensional shapes. Specific changes in SSVEP amplitude, phase and coherence are associated with a high aptitude for this task and these changes may be used to identify individuals with a high ability to manipulate three dimensional images. Studies undertaken by the inventor reveal that individuals with a high aptitude for the manipulation of three dimensional images exhibit a greater phase advance at left prefrontal cortical sites and reduced coherence between central and parietal cortical sites. By contrast, subjects with a high ability show increased SSVEP coherence between right prefrontal and central sites during the time that the image was held in short term memory without manipulation.

More particularly, the techniques of the invention can be used in a number of different fields including:

(i) identifying cognitive aptitude in specific domains;
(ii) identifying an individual's thinking style and hence the optimum teaching/training approach;
(iii) identifying the suitability of an individual for specific training; and
(iv) identifying the suitability of an individual for specific employment.

The changes in SSVEP amplitude, phase and/or coherence can be an increase or decrease. Also, the magnitude of the change may vary from case to case. One way of determining whether there has been a significant change in SSVEP amplitude, phase and/or coherence is by reference to statistical analyses where a change is regarded as significant at the $p<0.05$ level where p represents the probability of a Type 1 statistical error (i.e. wrongly rejecting the null hypothesis). Statistical significance can be tested using a number of methods including student's t-test, Hotellig's T2 and the multivariate permutation test. For a discussion of these methods used to analyse the SSVEP see Silberstein R. B., Danieli F., Nunez P. L. (2003) Frontoparietal evoked potential synchronisation is increased during mental rotation. Neuroreport, 14:67-71, Silberstein R. B., Farrow M. A., Levy F., Pipingas A., Hay D. A., Jarman F. C. (1998). Functional brain electrical; activity mapping in boys with attention deficit hyperactivity disorder. Archives of General Psychiatry 1998; 55:1105-12.

BRIEF DESCRIPTION OF THE DRAWINGS

The invention will now be further described with reference to the accompanying drawings, in which.

DETAILED DESCRIPTION OF THE INVENTION

Figure 1:
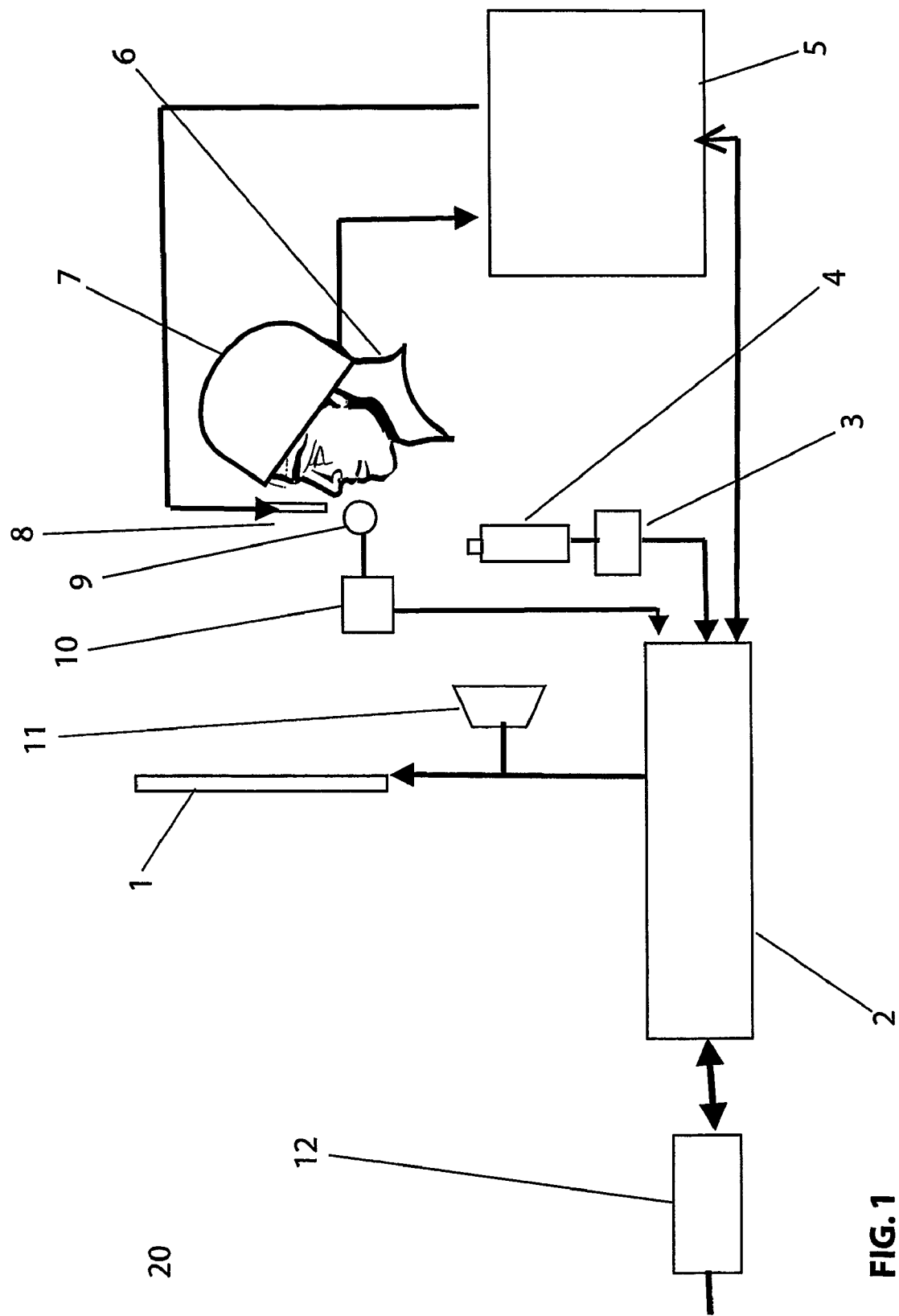
FIG. 1 is a schematic diagram of a system of the invention.

FIG. 1 schematically illustrates a system 20 for determining the response of a subject 6 to a cognitive task which can be presented to the subject 6 on a video screen 1 and loudspeaker 11. The system includes a computer 2 which controls various parts of the hardware and also performs computation on signals derived from the brain activity of the subject 6, as will be described below. The computer 2 also holds the cognitive task which can be presented to the subject 6 on the screen 1 and/or through the loudspeaker 11.

Figure 2:
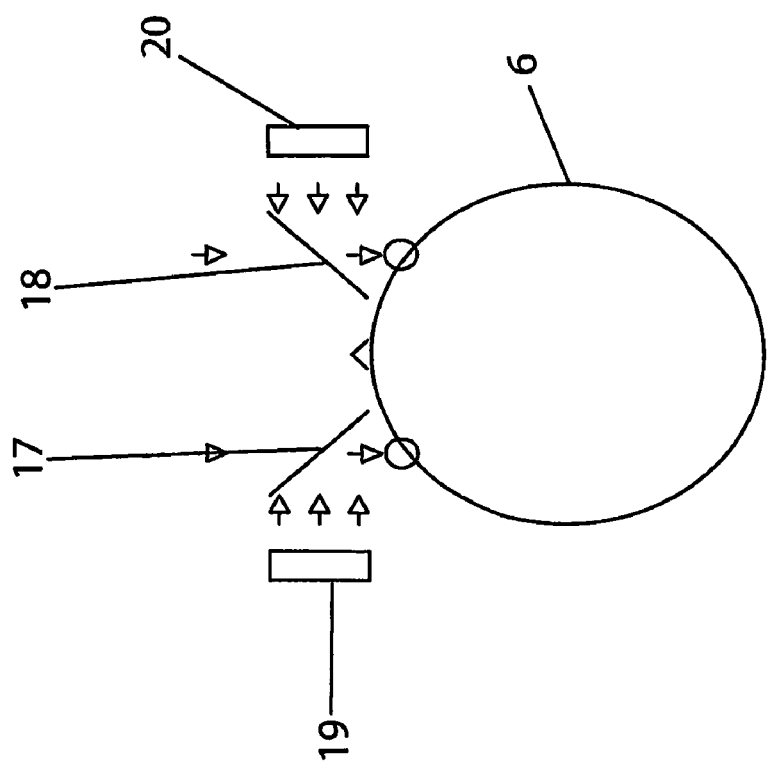
FIG. 2 is a schematic plan view showing in more detail the manner in which visual flicker signals are presented to a subject.

The subject 6 to be tested is fitted with a helmet 7 which includes a plurality of electrodes for obtaining brain electrical activity from various sites on the scalp of the subject 6. The helmet includes a visor 8 which includes half silvered mirrors 17 and 18 and LED arrays 19 and 21, as shown in FIG. 2. The half silvered mirrors are arranged to direct light from the LED arrays 19 and 21 towards the eyes of the subject. The LED arrays 19 and 21 are controlled so that the light intensity therefrom varies sinusoidally under the control of control circuitry 5. The control circuitry 5 includes a waveform generator for generating the sinusoidal signal. The circuitry 5 also includes amplifiers, filters, analogue to digital converters and a USB interface for coupling the various electrode signals into the computer 2.

The system also includes a microphone 9 for recording voice signals from the subject 6. The microphone 9 is coupled to the computer 2 via a microphone interface circuit 10. The system also includes a switch 4 which can be manually operated by the subject as a part of the response to the cognitive task. The switch 4 is coupled to the computer 2 via a switch interface circuit 3.

The computer 2 includes software which calculates SSVEP amplitude phase and/or coherence from each of the electrodes in the helmet 7.

Details of the hardware and software required for generating SSVEP are well known and need not be described in detail. In this respect reference is made to the aforementioned United States patent specifications which disclose details of the hardware and techniques for computation of SSVEP. Briefly, the subject 6 views the video screen 1 through the visor 8 which delivers a continuous background flicker to the peripheral vision. The frequency of the background flicker is typically 13 Hz but may be selected to be between 3 Hz and 50 Hz. Brain electrical activity will be recorded using specialised electronic hardware that filters and amplifies the signal, digitises it in the circuitry 5 where it is then transferred to the computer 2 for storage and analysis. SSPT is used to ascertain regional brain activity at the scalp sites using SSPT analysis software.

The cognitive tasks are presented on the video screen 1 and/or via the loudspeaker 11. The subject 6 is required to make a response that may comprise a button push on the switch 4 and/or a verbal response which is detected by the microphone 9. The topographic distribution of the SSVEP amplitude, SSVEP phase and SSVEP coherence during the performance of the cognitive tasks can be correlated with the aptitude and thinking style of the subject. The microphone 9 generates audio signals which are amplified, filtered and digitised via the interface 10 and stored as sound files on the computer 2. This enables the timing of the verbal responses to be determined within an accuracy of say 10 microseconds. Alternatively, the subject may respond to the cognitive task via a motor response such as a button push via the switch 4. In all cases, the precise timing of all events presented to the subject 6 are preferably determined with an accuracy of no less than 10 microseconds.

As mentioned above, the visor 8 includes LED arrays 19 and 21. In one embodiment, the light therefrom is varied sinusoidally. An alternative approach utilises pulse width modulation where the light emitting sources are driven by 1-10 Khz pulses where the pulse duration is proportional to the brightness of the sight emitting sources. In this embodiment, the control circuitry 5 receives a digital input stream from the computer 2 and outputs pulse width modulated pulses at a frequency of 1-10 Khz. The time of each positive going zero-crossing from the sinusoidal stimulus waveform is determined to an accuracy of 10 microsecond and stored in the memory of the computer 2.

Brain electrical activity is recorded using multiple electrodes in helmet 7 or another commercially available multi-electrode system such as Electro-cap (ECI Inc., Eaton, Ohio USA). The number of electrodes is normally not less than 16 and normally not more than 256, and is typically 64.

Brain activity at each of the electrodes is conducted to the control circuitry 5. The circuitry 5 includes multistage fixed gain amplification, band pass filtering and sample-and-hold circuitry for each channel associated with an electrode of the helmet. Amplified/filtered brain activity is digitised to 16 bit accuracy at a rate not less than 300 Hz and transferred to the computer 2 for storage on hard disk. The timing of each brain electrical sample together with the time of presentation of different components of the cognitive task are also registered and stored to an accuracy of 10 microseconds.

SSVEP Amplitude, Phase and Coherence

The digitised brain electrical activity (EEG) together with timing of the stimulus zero crossings enables calculation of the SSVEP from the recorded EEG or from EEG data that has been pre-processed using Independent Components Analysis to remove artefacts and increase the signal to noise ratio. [Bell A. J. and Sejnowski T. J. 1995. *An Information Maximisation Approach to Blind Separation and Blind Deconvolution*, Neural Computation, 7, 6, 1129-1159; T-P. Jung, S. Makeig, M. Westerfield, J. Townsend, E. Courchesne and T. J.

Sejnowskik, *Independent Component Analysis of Single-Trial Event-Related Potential Human Brain Mapping*, 14(3):168-85, 2001.]

Calculation of SSVEP amplitude and phase for each stimulus cycle can be accomplished using Fourier techniques using equations 1.0 and 1.1 below:

$$a_n = \frac{1}{S\Delta\tau}\sum_{i=0}^{S-1} f(nT + i\Delta\tau)\cos\left(\frac{2\pi}{T}(nT + i\Delta\tau)\right) \quad \text{Equation 1.0}$$

$$b_n = \frac{1}{S\Delta\tau}\sum_{i=0}^{S-1} f(nT + i\Delta\tau)\sin\left(\frac{2\pi}{T}(nT + i\Delta\tau)\right)$$

Where $a_n$ and $b_n$ are the cosine and sine Fourier coefficients respectively. n represents the nth stimulus cycle, S is the number of samples per stimulus cycle (16), $\Delta\tau$ is the time interval between samples, T is the period of one cycle and $f(nT+i\Delta\tau)$ is the EEG signal (raw or pre-processed using ICA).

$$SSVEP_{amplitude} = \sqrt{(a_n^2 + b_n^2)} \quad \text{Equation 1.1}$$

$$SSVEP_{phase} = a\tan\left(\frac{b_n}{a_n}\right)$$

Amplitude and phase components can be calculated using either single cycle Fourier coefficients or coefficients that have been calculated by integrating across multiple cycles.

Two types of coherence functions are calculated from the SSVEP sine and cosine Fourier coefficients while subjects undertake the cognitive task. One will be termed the SSVEP Coherence ("SSVEPC") and the other, Event Related SSVEP Coherence ("ER-SSVEPC").

SSVEPC

The SSVEP sine and cosine coefficients can be expressed as complex numbers $$C_n = (a_n, b_n)$$

where $a_n$ and $b_n$ have been previously defined.

The nomenclature is generalised to take into account multiple tasks and multiple electrodes.

$$C_{g,e,n} = (a_{g,e,n}, b_{g,e,n})$$

where
 g=the task number
 e=the electrode
 n=the point in time

The following functions are defined:

$$\gamma_{g,e1,e2} = \frac{H_{g,e1,e2}}{T_{g,e1,e2}} \quad \text{Equation 1.2}$$

$$H_{g,e1,e2} = \sum_{n=1}^{n=T} C_{g,e1,n} \cdot C^*_{g,e2,n}$$

Where C* is the complex conjugate of C and $$T_{g,e1,e2} = \sqrt{\left(\sum_{n=1}^{T} C_{g,e1,n} \cdot C^*_{g,e1,n}\right)\left(\sum_{n=1}^{T} C_{g,e2,n} \cdot C^*_{g,e2,n}\right)} \quad \text{Equation 1.3}$$

The SSVEPC is then given by $$\gamma^2_{g,e1,e2} = \frac{|H_{g,e1,e2}|^2}{T^2_{g,e1,e2}} \quad \text{Equation 1.4}$$

And the phase of the SSVEPC is given by ER-SSVEPC $$\phi_{g,e1,e2} = \text{Tan}^{-1}\left(\frac{\text{Im}(H_{g,e1,e2})}{\text{Re}(H_{g,e1,e2})}\right) \quad \text{Equation 1.5}$$

In this case, the coherence across trials in a particular task can be calculated. This yields coherence as a function of time. The nomenclature can be generalised to take into account multiple tasks and multiple electrodes.

$$C_{g,d,e,n} = (a_{g,d,e,n}, b_{g,d,e,n})$$

where
 g=the task number
 d=the trial within a particular task, eg a specific response
 e=the electrode
 n=the point in time The following functions are defined:

$$\gamma_{g,e1,e2,n} = \frac{H_{g,e1,e2,n}}{T_{g,e1,e2,n}} \quad \text{Equation 1.6}$$

$$H_{g,e1,e2,n} = \sum_{d=1}^{d=D} C_{g,e1,d,n} \cdot C^*_{g,e2,d,n}$$

and $$T_{g,e1,e2,n} = \sqrt{\left(\sum_{d=1}^{D} C_{g,e1,d,n} \cdot C^*_{g,e1,d,n}\right)\left(\sum_{d=1}^{D} C_{g,e2,d,n} \cdot C^*_{g,e2,d,n}\right)} \quad \text{Equation 1.7}$$

The SSVEPC is then given by $$\gamma^2_{g,e1,e2,n} = \frac{|H_{g,e1,e2,n}|^2}{T^2_{g,e1,e2,n}} \quad \text{Equation 1.8}$$

And the phase of the SSVEPC is given by $$\phi_{g,e1,e2,n} = \text{Tan}^{-1}\left(\frac{\text{Im}(H_{g,e1,e2,n})}{\text{Re}(H_{g,e1,e2,n})}\right) \quad \text{Equation 1.9}$$

The above equations apply to scalp recorded data as well as brain electrical activity inferred at the cortical surface adjacent to the skull and deeper such as the anterior cingulate cortex. Activity in deeper regions of the brain such as the anterior cingulate or ventro-medial cortex can be determined using a number of available inverse mapping techniques such as BESA (Scherg M, Ebersole J S., *Brain Source Imaging of Focal and Multifocal Epileptiform EEG Activity. Neurophysiol Clin.* 1994 January; 24(1):51-60); LORETA (Pascual-Marqui RD, Esslen M, Kochi K, Lehmann D. *Functional Imaging with Low-Resolution Brain Electromagnetic*

Tomography (LORETA): A Review. Methods Find Exp Clin Pharmacol. 2002; 24 Suppl C:91-5); or EMSE Information (Source Signal Imaging Inc. 2323 Broadway, Suite 102, San Diego, Calif. 92102).

While the subject 6 is performing the cognitive and emotional tasks, the visual flicker is switched on in the visor 8 and brain electrical activity is recorded continuously on the computer 2.

At the end of the tests, the SSVEP responses associated with the various tasks can be calculated and separately averaged. For specific tasks, the SSVEP amplitude, phase and coherence can be compared with a database of results for groups of subjects with high aptitude and specific thinking styles. The comparison will identify the individuals specific thinking style and aptitude. For example, individuals with an aptitude for computer software development may demonstrate increased SSVEP phase lag at prefrontal sites and reduced left frontal SSVEP coherence while performing Raven's Progressive Matrices (a task used in IQ tests). By contrast, an individual suited as an aircraft pilot may demonstrate reduced left temporal SSVEP coherence when performing the mental rotation task. For security purposes, the database can be situated on a remote computer (not shown) accessed via the internet through a modem 12.

EXAMPLE 1

Figure 3:
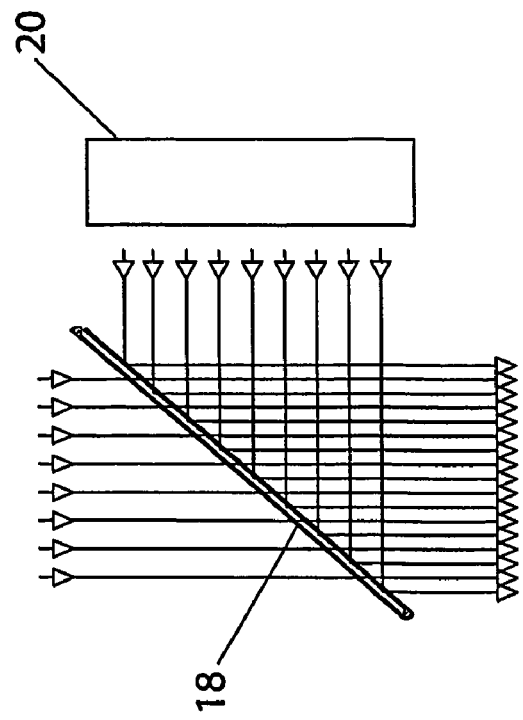
FIG. 3 is a schematic view showing one of the half silvered mirrors and LED array.

The system illustrated in FIGS. 1 to 3 was used for testing subjects using an analytical test known as the Hidden Figures Test. Data from the electrode sites was analysed using the SSPT technique based on computer algorithms listed in Equation 1.1 and the SSVEP phase distribution was displayed graphically.

Figure 4:
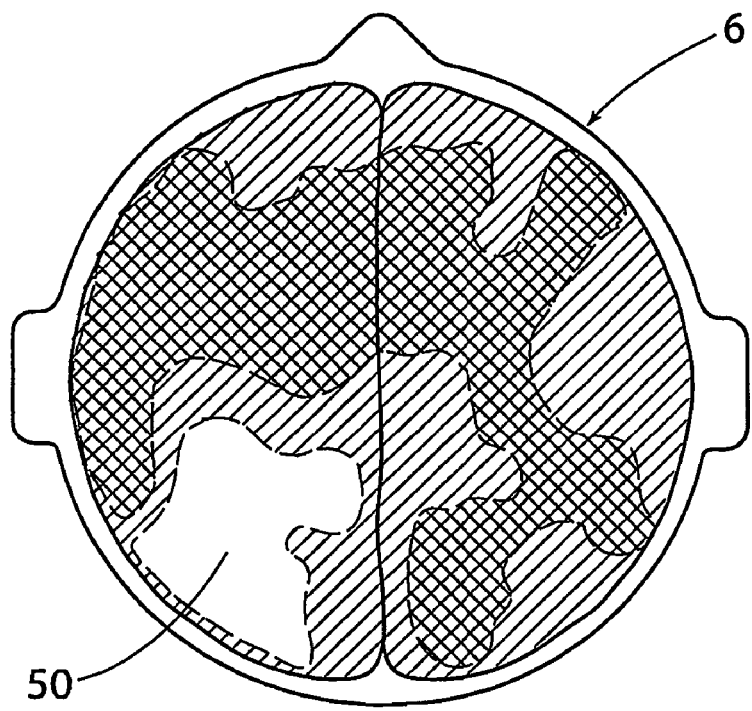
FIG. 4 diagrammatically illustrates SSVEP phase distribution for a subject with high analytical aptitude.

FIG. 4 illustrates the SSVEP phase from a subject having high analytical aptitude. In this Figure, the lighter areas represent SSVEP phase advance or regions of increased brain processing speed. In this diagram, the darker shades represent SSVEP phase lag or regions of reduced brain processing speed. The light area 50 delineated in broken lines demonstrates and area of greater activation. This area is situated in the posterior left hemisphere in the region of the temporal and parietel cortex. This indicates that the subject has a high analytical aptitude.

Figure 5:
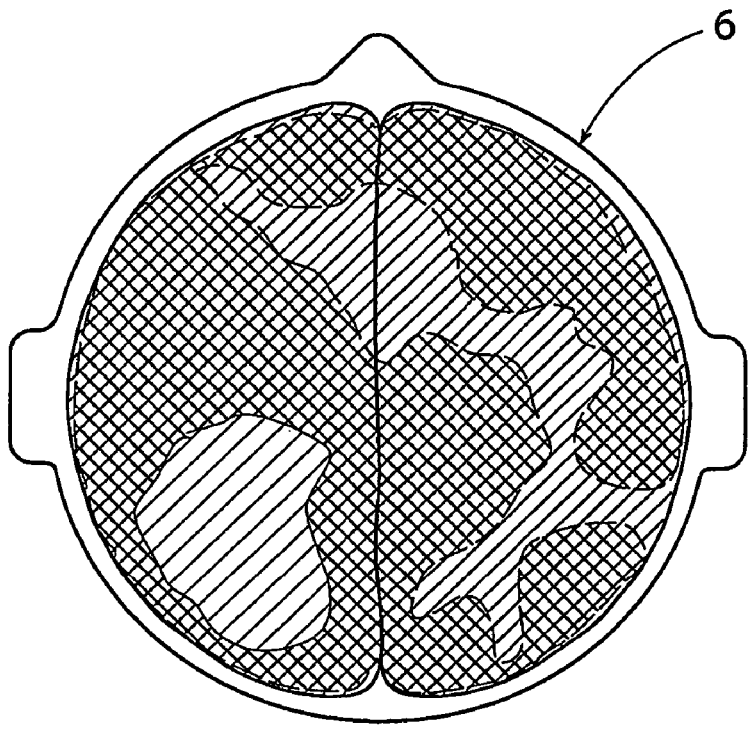
FIG. 5 diagrammatically illustrates SSVEP phase distribution where the subject has a low analytical aptitude.

FIG. 5 graphically represents the SSVEP phase distribution for a subject carrying out the same test. It will be noted that there are no light areas in the distribution and this distribution is interpreted as demonstrating that the subject has low analytical aptitude.

EXAMPLE 2

The same equipment was used as in Example 1 above but the subjects were made to perform the Gestalt Completion Test. The Gestalt Completion Test places demands on holistic thinking. Electrical activity from the electrode sites was analysed using the SSPT technique based on computer algorithms listed in Equation 1.1 and the results displayed graphically.

Figure 6:
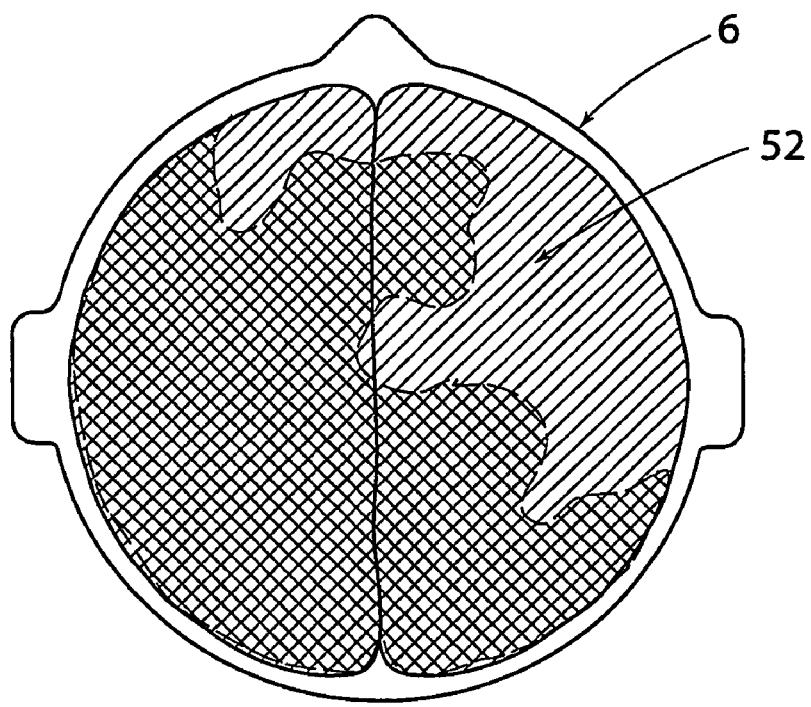
FIG. 6 diagrammatically illustrates SSVEP phase distribution for subjects with high holistic thinking capacity.

FIG. 6 diagrammatically shows SSVEP phase distribution. The results include a light area 52 bounded by broken lines. This light area demonstrates increased activity in the right temporal and right frontal areas which is consistent with the importance of right hemisphere activity in holistic recognition. This is interpreted as indicating that the subject has high holistic thinking ability.

Figure 7:
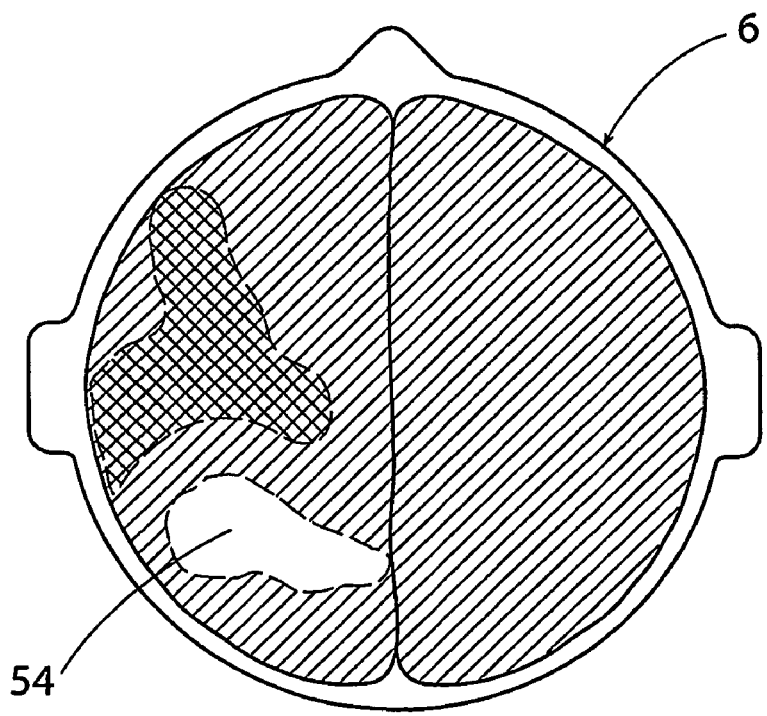
FIG. 7 diagrammatically illustrates SSVEP phase distribution for subjects with low holistic thinking capacity.

FIG. 7 in contrast shows the results of a subject performing the same test for a subject having low holistic thinking abilities. The SSVEP phase distribution shows reduced left temporal activity and enhanced left parietal, left posterior activity as indicated by the light area 54 bounded by broken lines.

EXAMPLE 3

The system shown in FIGS. 1 to 3 was used to test subjects carrying out a computerised version of Raven's Progressive Matrices. Electrical activity was again processed using the SSPT technique based on computer algorithms listed in Equation 1.8. The results are displayed graphically in FIGS. 8 and 9.

Figure 8:
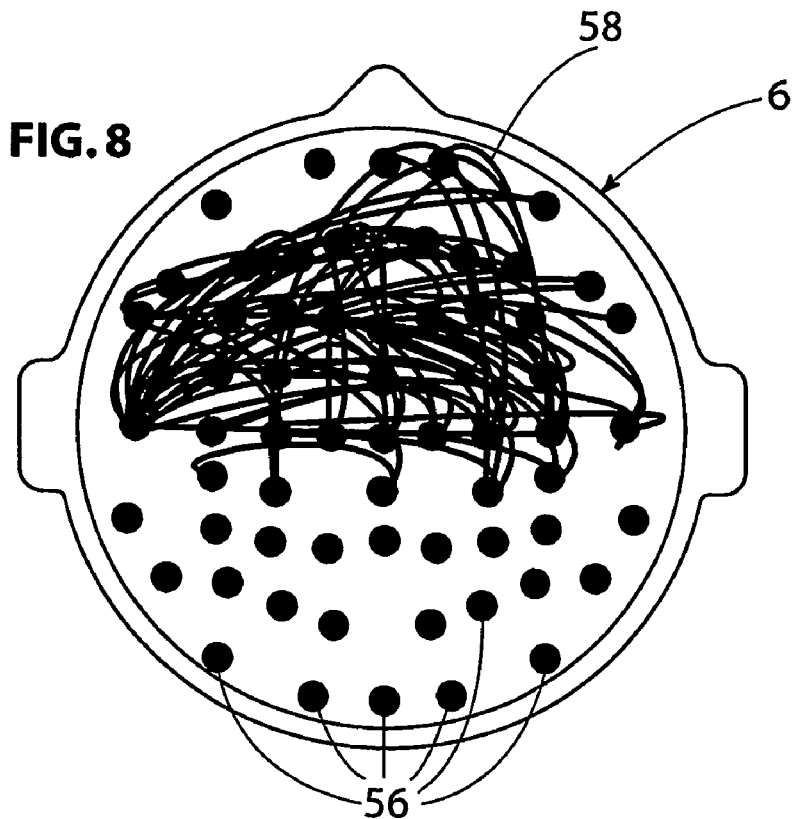
FIG. 8 diagrammatically illustrates SSVEP coherence at frontal sites for subjects having high verbal IQ.

The graph of FIG. 8 shows event related SSVEP coherence between activity recording sites 56. The display includes a plurality of lines 58 between frontal sites. This result was produced from statistically significant differences in event related SSVEP coherence recorded from participants having high verbal IQ scores.

Figure 9:
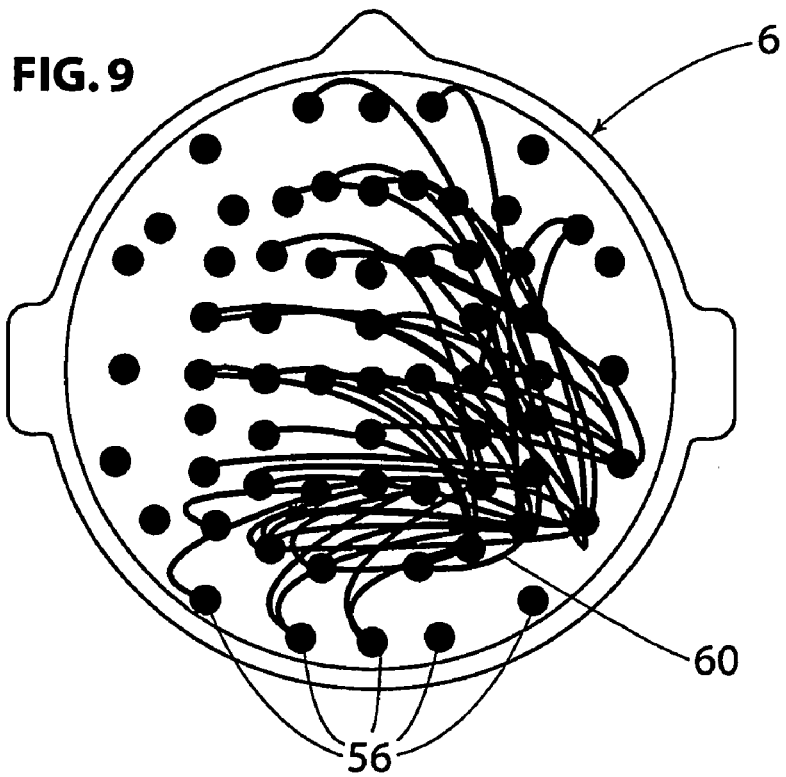
FIG. 9 diagrammatically illustrates SSVEP coherence in subjects having high conceptual and visualisation skills.

FIG. 9 graphically illustrates statistically significant differences in event related SSVEP coherence recorded from participants having high conceptual and visualisation skills (performance IQ). The results graphically shown in FIG. 9 include lines 60 demonstrating increased event related SSVEP coherence between right parieto-temporal regions and other scalp sites. The activity was measured whilst the subjects were preparing to make decisions while undertaking a computerised version of Raven's Progressive Matrices.

With the techniques of the invention, by examining the scalp distribution of the SSVEP phase and amplitude and SSVEP event related coherence during a range of thinking tasks and by comparing these distributions with a database of known SSVEP amplitude, phase and coherence patterns, it is possible to infer the aptitude of a specific participant to various tasks.

Many modifications will be apparent to those skilled in the art without departing from the spirit and scope of the invention.

The invention claimed is:

1. A method of assessing the cognitive aptitude of a subject to a predetermined task, the method including the steps of:
   (i) simultaneously presenting to the subject one of a group of cognitive tasks and a visual flicker;
   (ii) detecting brain response signals from the subject during presentation of said cognitive task and visual flicker;
   (iii) calculating amplitude, phase and/or coherence of SSVEP responses elicited by the visual flicker from said brain response signals; and
   (iv) comparing said SSVEP responses to known SSVEP responses obtained from individuals with high and/or low aptitudes to said predetermined task in order to assess the subject's aptitude for said predetermined task.

2. A method as claimed in claim 1 wherein including the step of presenting said group of cognitive tasks to said individuals in order to obtain said known SSVEP responses and storing said known SSVEP response in a database.

3. A method as claimed in claim 1 or 2 wherein the cognitive tasks are selected so that they place demands on the subject which are similar to demands experienced when carrying out the predetermined task.

4. A method as claimed in claim 3 wherein the cognitive tasks are selected so that they place one or more of the following demands on the subject: attention, analytical thinking, holistic thinking, verbal thinking, visuo-spatial thinking, working memory, recognition memory and identifying emotional expressions.

5. A method as claimed in claim 1 including the steps of:
repeating the presentation of said cognitive tasks in order to calculate multiple SSVEP responses;
statistically analysing said SSVEP responses in order to determine statistically significant changes in SSVEP amplitude, phase and/or coherence; and
comparing said statistically significant changes to said known SSVEP responses in order to assess the subject's aptitude for said predetermined task.

6. A method as claimed in claim 1 wherein the step of comparing said SSVEP responses to known SSVEP responses includes the step of assessing the subject's thinking style.

7. A method as claimed in claim 1 wherein steps (i), (ii) and (iii) are performed at a local site and wherein step (iv) is performed at a remote site.

8. A method as claimed in claim 7 including the step of maintaining a database of said known SSVEP responses at said remote site.

9. A method as claimed in claim 8 including the step of communicating the amplitude, phase and/or coherence SSVEP responses from the local site via the Internet to said remote site.

10. Apparatus for assessing the cognitive aptitude of a subject to a predetermined task, the apparatus including:

(i) means for simultaneously presenting to the subject one of a group of cognitive tasks and a visual flicker;
(ii) means for detecting brain response signals from the subject during presentation of said cognitive task and visual flicker;
(iii) means for calculating amplitude, phase and/or coherence of SSVEP responses elicited by the visual flicker from said brain response signals; and
(iv) means for comparing said SSVEP responses to known SSVEP responses obtained from individuals with high and/or low aptitudes to said predetermined task in order to assess the subject's aptitude for said predetermined task.

11. Apparatus as claimed in claim 10 wherein said means for presenting, said means for detecting and said means for calculating are located at a local site and said means for comparing is located at a remote site and wherein the apparatus includes coupling means for coupling said means for calculating to a communications network for transmitting said SSVEP amplitude, phase and/or coherence responses to said means for comparing via the network.

12. Apparatus as claimed in claim 11 wherein the coupling means includes a modem and the network is the Internet.

* * * * *